US00PP10954P

United States Patent [19]

Janecek

[11] Patent Number: Plant 10,954

[45] Date of Patent: Jun. 8, 1999

[54] VARIETY OF GERANIUM PLANT NAMED 'EVKA'

[75] Inventor: Jaroslav Janecek, Vrbové, Slovakia

[73] Assignee: Elsner pac Jungpflanzen, Germany

[21] Appl. No.: 08/877,275

[22] Filed: Jun. 17, 1997

[51] Int. Cl.[6] ..... A01H 5/00

[52] U.S. Cl. ..... Plt./87.12

[58] Field of Search ..... Plt./87.12

[56] References Cited

PUBLICATIONS

UPOV–ROM,Germany, PBR PEL 00979, Pelargonium 'Evka', 1995.

UPOV–ROM, Great Britain, PBR 03600282, Pelargonium 'Evka', 1995.

UPOV–ROM, Israel, PBR 02482, Pelargonium 'Evka', 1995.

*Primary Examiner*—Howard J. Locker

*Assistant Examiner*—Melissa L. Kimball

*Attorney, Agent, or Firm*—Webb Ziesenheim Bruening Logsdon Orkin & Hanson, P.C.

[57] ABSTRACT

A new and distinct variety of Ivy Geranium having a variegated green and white foliage color. The leaves exhibit minimal leaf cupping. The cutting production is good with the rooting speed and propagation survival rate being very good. The neat cascading ball form and the medium size growth allow ease in shipping and handling.

1 Drawing Sheet

BACKGROUND OF THE NEW PLANT

The present invention comprises a new and distinct cultivar of *Pelargonium x peltatum* known by the varietal name 'Evka' (Oglevee, Ltd. No. 5223). The new variety was discovered in the Slovakian Republic in February of 1994 and was first asexually reproduced in January of 1995. It is a mutation of the unpatented variety 'Ville der Paris'. The new variety was first asexually reproduced in the United States at Oglevee, Ltd., 152 Oglevee Lane, Connellsville, Pa. in January of 1996. It has been found to retain its distinct characteristics through successive propagations.

The new cultivar, when grown in a glass greenhouse in Connellsville, Pa., using full light, 60° F. night temperature, 68° F. day temperature, 72° . vent, and grown in a soilless media with constant fertilizer of 200–250 parts per million calcium nitrate and potassium nitrate, has a response time from a rooted cutting to a flowering plant in 10 cm. pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted and then flowered six weeks later. The plant histories were taken of plants blossomed under full light in a greenhouse and color readings were taken indoors under 200–220 foot candles of cool white fluorescent light. The full light was that of the winter months with color readings being taken in early February. Spring or summer light conditions will result in an inflorescence coloring having a more true shade of red. Color references are primarily to the R.H.S. Colour Chart of The Royal Horticultural Society of London.

THE PLANT

Classification:

*Botanical.*—*Pelargonium x peltatum.*

*Commercial.*—Ivy Geranium named 'Evka'.

Form: Medium cascading mound.

Height: 10 to 13 cm. from top of pot.

Growth: Free and early flowering; very free branching; cascading.

Foliage: Green and white variegated leaf; stalked leaf attachment.

Leaves:

*Size.*—3.0 to 3.5 cm long; 4.0 to 5.0 cm wide.

*Shape.*—Reniform, cordate base.

*Margin.*—Pedately lobed; slightly serrated.

*Texture.*—Slightly pubescent.

*Color.*—Top: Green Group 137C; Margin: Green-White Group 157C — white margin is more predominant on some leaves than on others. Mature leaves have a silvery glisten when observed closely. Bottom: Yellow-Green Group 148B; Margin: Green-White Group 157C.

*Ribs and veins.*—Venation: Palmate. Color: Yellow-Green Group 147B.

Petioles:

*Length.*—2 to 4.5 cm.

*Color.*—Yellow-Green Group 146B; some petioles have a slight stripe of Green-White Group 157C.

Stem:

*Color.*—Yellow-Green Group 146B; stipules are variegated green and white.

*Internodes.*—2 to 3.5 cm. in length.

THE BUD

Shape: Elliptical cluster; 5–9 buds per umbel.

Size: 1.5 to 2 cm. across.

INFLORESCENCE

Blooming habit: Upright; continuous; free and early flowering.

Borne: Florets on pedicel; pedicel on peduncle; umbel 4 to 7 cm. above foliage canopy.
Closed florets: Bud size: 1 to 1.2 cm. in length; 0.4 to 0.5 cm. in width.
Size: Fully Open Bloom: 6 to 8.5 cm. across.
Open florets:
*Form.*—Single, flat to a "reverse cup" with petals turning backwards.
*Color.*—Top: Red Group 40B — upper two petals have a veining of Red-Purple Group 59B. Bottom: Red Group 43C.
Petals: Margin entire; separate, not united; five in number. Sepals behind petals are also green and white variegated.
Size: 3 to 3.5 cm. across.
Texture and appearance: Single floret containing five petals; appearance is a soft muted red.
Petaloids: Quantity: None observed.
Pedicel:
*Length.*—2.5 to 3 cm.
*Color.*—Shading of Greyed-Purple Group 183C over Yellow-Green Group 146A.
Peduncle:
*Length.*—10.5 to 12.5 cm.
*Color.*—Yellow-Green Group 146B.
Disease resistance: Not known.
Lasting quality: The single florets hold together for 7 to 14 days indoors, which is longer than other varieties of this type and this variety is quick to reflower.

REPRODUCTIVE ORGANS

Stamens:
*Anthers.*—2 to 3 mm. in length.
*Filaments.*—5 to 6 cm. in length, white in color.
*Pollen.*—Golden Brown.
Pistils:
*Number.*—1.
*Length.*—1 to 1.3 cm.
*Stigma.*—White to very pale pink in color.
Style.—4 to 5 mm. in length.
*Ovaries.*—Color: White to very pale green; pubescent. Length: 5 to 6 mm.
Fruit: None observed.

GENERAL CHARACTERISTICS

A new geranium that is a unique new addition to the group of "mini-cascade" ivy geraniums. The variegated green and white foliage color is outstanding in uniformity. This variety also exhibits much less leaf cupping which is a problem in variegated geraniums of this type. Cutting production is equal to or better than the current market variety 'Mini Cascade Red' also known as "Rotemica" (unpatented). Rooting speed and propagation survival rate are both very good. As a finished product this variety produces a neat cascading ball in a hanging basket and the medium size growth habit allows ease in shipping and handling.

I claim:

1. A new and distinct variety of Ivy Geranium plant as shown herein and characterized by its uniform green and white foliage, its minimal leaf cupping, its improved cutting production, rooting speed and propagation survival rate and its cascading appearance and coloration.

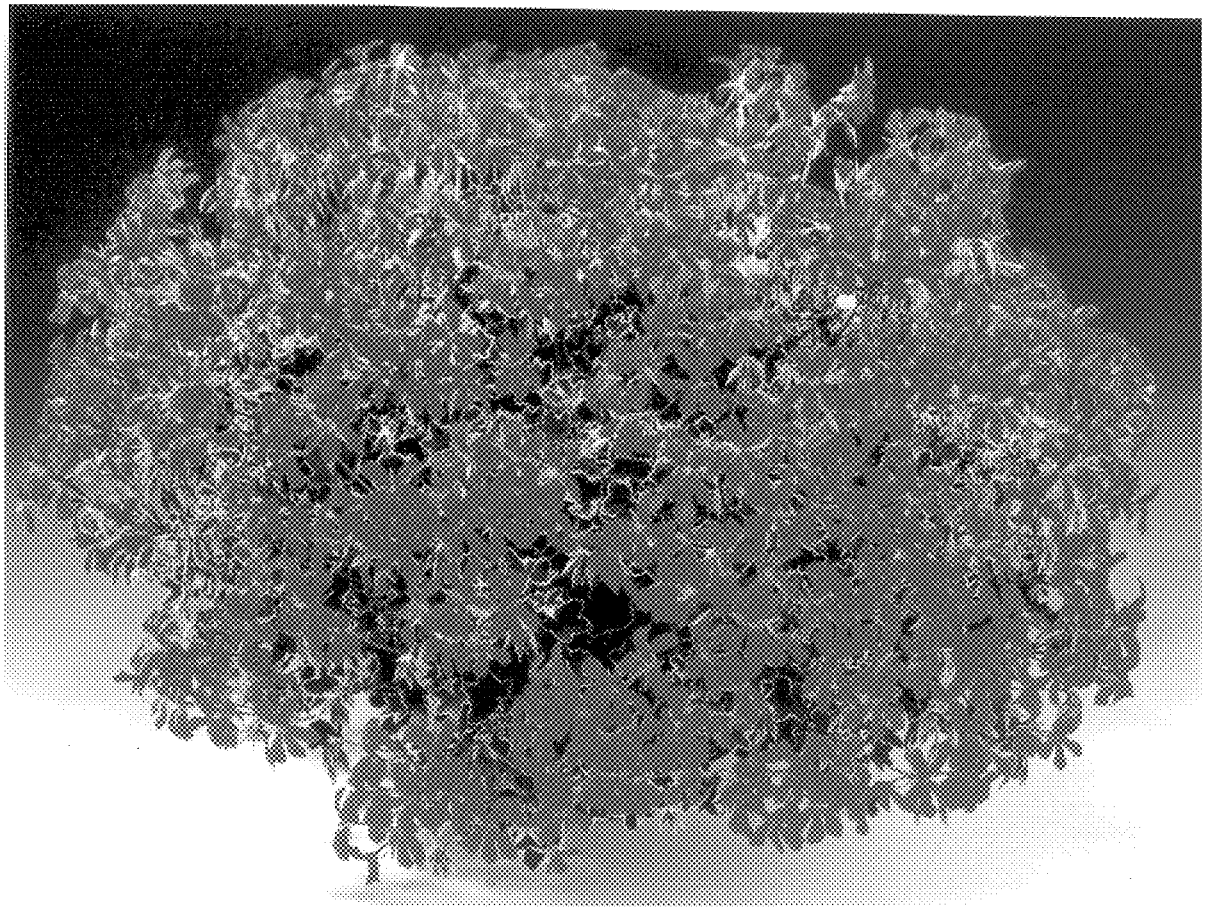

* * * * *